(12) United States Patent
Cole

(10) Patent No.: US 6,776,485 B2
(45) Date of Patent: Aug. 17, 2004

(54) APPARATUS FOR ATTACHING SPECTACLES TO A FACIAL MASK

(76) Inventor: Anthony John Cole, 16 Trevalsa Place, Burraneer, New South Wales (AU), 2230

( * ) Notice: Subject to any disclaimer, the term of this patent is extended or adjusted under 35 U.S.C. 154(b) by 73 days.

(21) Appl. No.: 09/874,571

(22) Filed: Jun. 5, 2001

(65) Prior Publication Data

US 2004/0109131 A1 Jun. 10, 2004

(51) Int. Cl.[7] ................................................. G02C 1/00
(52) U.S. Cl. ...................................... 351/158; 248/902
(58) Field of Search ................ 351/41, 158; 248/309.1, 248/902

(56) References Cited

U.S. PATENT DOCUMENTS 5,979,849 A * 11/1999 Williams .................... 248/902

* cited by examiner

Primary Examiner—Hung Xuan Dang
(74) Attorney, Agent, or Firm—Jacobson & Johnson

(57) ABSTRACT

Eyewear assembly for mounting eyewear to facial apparatus which includes a spectacle body, mounting means for holding the spectacle body in a mounted position on the facial apparatus, the mounting means including resilient members adapted to co-operate with a mounting element to hold the spectacle body in the mounted position.

10 Claims, 2 Drawing Sheets

APPARATUS FOR ATTACHING SPECTACLES TO A FACIAL MASK

FIELD OF THE INVENTION

The present invention relates to an eyewear mounting arrangement. and in particular, hut not exclusively, an arrangement which will enable eyewear to be worn in conjunction with other facial apparatus such as a breathing mask

BACKGROUND OF THE INVENTION

There are numerous people who for one reason or another are required to Wear facial apparated Which because of the shape and positioning prevent, or impair, The person from utilizing, spectacles. For example many people who suffer from disorders such as sleep apnoea, asthina or emphysema, or simply people who are old or infirm utilise facial masks to deliver oxygen, air or positive airway p c sur to the nose, month or both. Because of the arrangement of such breathing masks, it is very often the case that conventional spectacles, which may be necessary for reading or watching television cannot be worn. As readily understood, conventional spectacles are hold in place by side arms which rest upon the ears in conjunction with a bridge which rests on the bridge of the nose. As many facial masks for breathing apparats cover the nose entirely, conventional spectacles, which rest upon the bridge of the nose cannot be used.

Especially in the case of sleep apnoea, which requires the use of a facial mask to apply positive pressure to the airways to thereby prevent airway collapse during sleep, it is necessary only for lie apparatus to be worn during sleeping hours. Many patients however, wish to read just prior to falling off to sleep to aid the transition into a sleeping state.

Up until the present time it has been necessary for the patient to finish their reading, remove their spectacles. fit the facial mask and turn the respiration machine on, before then attempting to fall to sleep. Many patients complain that after having carried out these activities they no longer feel sleepy, and that accordingly it Would be beneficial if there was a means by which they could wear their spectacles at the same time as the facial mask.

It should he understood that the present invention has utility not only in relation to the use of spectacles in conjunction with facial respiratory masks. but also in relation to other facial apparatus. For example, the present invention may also be useful when wearing prescription spectacles in conjunction with protective eyewear such as swimming masks or safety goggles or masks of various descriptions. It is important however, that the facial apparatus with which the spectacles are to be used in conjunction can be fastened to the facial region by one means or the other. The reason for this is that if the spectacles are to be attached to the facial apparatus, they will not be useful if they are able to significantly move about as a result of their platform, the facial apparatus. also having free movement.

It is an object of the present invention to provide an arrangement which will allow spectacles to be utilised in conjunction with facial apparatus which may otherwise impair their use. Other objects of the present invention will become apparent from the following detailed description thereof.

SUMMARY OF THE INVENTION

According to the present invention there is provided eyewear assembly for mounting eyewear to facial apparatus, the assembly including a spectacle body, mounting means for holding the spectacle body in a mounted position on the facial apparatus, the mounting means including resilient members adapted to co-operate with a mounting element to hold the spectacle body in the mounted position.

In one preferred embodiment the spectacle body includes a mounting cam thereon which defines the mounting element. The mounting means includes a mounting bracket which is securable to or integral with the facial apparatus the resilient members being part of the mounting bracket and including a mounting section and the pair of resilient members each having a retaining element at their free end portions. The arrangement is such that the mounting cam is insertable into the region between the resilient members in a first orientation and is thereafter rotated to an in-use position whereupon the retaining elements inhibit ready removable of the mounting cam therefrom.

In another preferred embodiment the mounting means includes a mounting bracket having a mounting section, the resilient members forming part of the mounting section and being adapted to snap fit onto a section of the facial apparatus which defines the mounting element.

In the first mentioned embodiment the spectacle body preferably includes a spectacle frame having two viewing sections and a bridge section which extends between the viewing sections. Preferably, the mounting cam is defined by the bridge section.

In the second embodiment the spectacle body includes a spectacle frame which includes two viewing sections which are interconnected by he resilient members. Preferably the resilient members extend from respective viewing section and terminate in a region which defines a mounting zone for receiving the mounting element therein in snap fit fashion. Preferably, there is further provided a gripping tab in the region of said mounting zone. Preferably, the viewing sections of the spectacle body are disposed generally in a plane which, when the spectacle body is in a fitted position is inclined with respect to an upright position.

BRIEF DESCRIPTION OF THE DRAWINGS

Preferred embodiments of the present invention will now be described with reference to the following drawings wherein:

FIG. 1A shows the bridging piece (shaded) about to be inserted between the members FIG. 1B shows the bridging piece inserted between the members and FIG. 1C shows the bridging piece retained between the members following rotation of the spectacles;

FIG. 4 is a front elevation of eyewear according to another aspect of the invention:

FIG. 5 is a side elevation view of the eyewear shown in FIG. 4: and.

DETAILED DESCRIPTION OF THE PREFERRED EMBODIMENT

Figure 1:
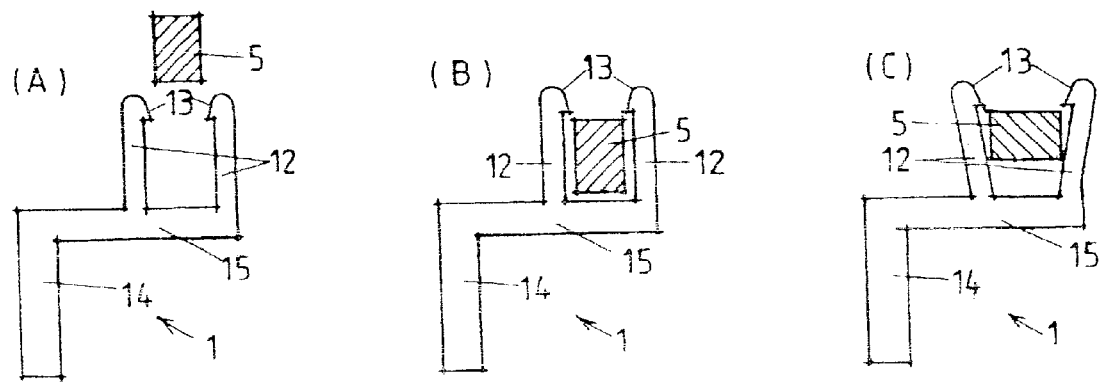
FIG. 1 shows a diagrammatic side view of the mountable bracket according to one aspect of the invention
Figure 2:
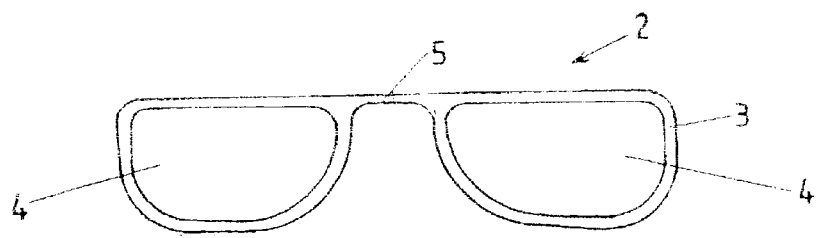
FIG. 2 shows a diagrammatic representation of the spectacles according to the invention, from the front.
Figure 3:
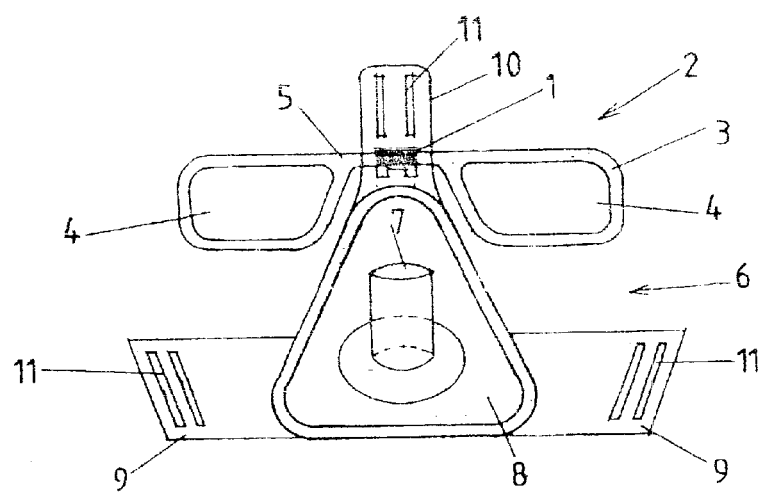
FIG. 3 shows a view from in front, of the spectacles and bracket according to the invention in place on a facial breathing mask.

The eyewear mounting arrangement according to the present invention as shown in FIGS. 1 to 3 is comprised of two major components, the mountable bracket 1 and the spectacles 2. Referring to FIG. 2, the spectacles 2 are comprised of a frame 3 which is adapted to receive a pair of lenses 4. The portion of the frame which joins together the two sections which hold the respective lenses is the bridging piece 5. It is this bridging piece 5 which is adapted to engage with the bracket 1 in order for the spectacles to he held in place on a facial apparatus. An example of such facial apparatus 6 is shown in FIG. 3. In this case the facial apparatus 6 is a breathing mask which is designed to be used in conjunction with a continuous positive airway pressure (CPAP) machine for the treatment of sleep apnoea. As can he seen from FIG. 3, the facial apparatus 6 includes an air vent 7 which is in communication with the CPAP machine. The air vent 7 leads into a reservoir 8 which on Its rear surface is comprised of flexible material for forming a substantially airtight seal against the patient's face. surrounding the nose. The facial apparatus also includes two side projections 9 and an upper projection 10, which are each equipped with slits 11, through which attachment straps can be connected. These attachment straps are used to securely fasten the facial apparatus to the patient's face. Naturally there are many means by which facial apparatus can be secured in position, another example is a cap or band which fits over the cranium.

As can also be seen from the example of the invention shown in FIG. 3, the bracket 1 is attached to the upper projection 10, and in turn the spectacles 2 are engaged within the bracket 1. The bracket 1 however, can be mounted in other positions as long as when engaged within the bracket 1 the spectacles 2 are in a position which is appropriate to aid the patient's vision.

It must be understood, as explained above, that the facial apparatus shown in FIG. 3 is simply one example of the facial apparatus in relation to which the present invention has utility. Other examples of a facial apparatus in relation to which the inventive eyewear mounting arrangement can he used include other breathing masks which may surround the nose or the nose and mouth. protective goggles or masks or other facial apparatus which interfere with the functioning of conventional spectacles The means by which the spectacles 2 are attachable to the mountable bracket 1 is that the bridging piece 5 of the spectacles 2 forms a cam The orientation of the cam is dependent upon the orientation of the mountable bracket 1, but in the situation where the mountable bracket 1 is mounted with the resilient members 12 pointing in an upward direction (directions are given relative to the position of the spectacles when in use, on a person who is standing or seated), the horizontal cross-sectional length of the bridging piece 5 would be greater than the vertical cross-sectional length of the bridging piece 5. In this way the spectacles 2 could be engaged on to the mounting bracket 1 by turning them so that they face upwardly and then sliding the bridging piece 5 between the resilient members. Rotating the spectacles about their longitudinal axis through 90° will then bring the camming action of the bridging piece 5 into play, to deform the resilient members 12. As a result of the inward force exerted on the bridging piece 5 by each of the resilient members 12, and the presence of opposing end restraints 13 on each of the resilient members 12, the bridging piece 5 will be held secure in position.

The spectacles 2 can then easily be removed by conducting the reverse operation and rotating through 90° and then withdrawing the bridge piece 5 from between the resilient members 12.

In the depiction of the mountable bracket 1 shown in FIG. 1, the mounting section 14 is simply a panel extending away from a base plate 15, from which in turn the resilient members 12 also extend. It should be understood however, that this is simply one possible embodiment of the invention and that there may not in fact be a separate mounting section 14, so that the base plate 15 may be utilised for mounting purposes. In another possibility, a mounting section 14 may extend upwardly, from the base plate 15, in the same direction as the resilient members 12.

The means by which the mountable bracket is in fact mounted upon a facial apparatus are many and varied. For example, the use of a screw or bolting arrangement, perhaps utilising nylon screws, could be adopted. The mountable bracket can in fact be formed integrally within a portion of the facial apparatus or can be applied by the use of an adhesive cement, heat welding, or other techniques well known in the art. Clearly however, attachment between the mountable bracket 1 and the facial apparatus 6 must be of reasonable strength, to prevent unwanted detachment of the components.

It is also to be understood that the resilient members 12 may project in any direction, as long as they are opposed, to thereby form a bracket about which the bridging piece 5 can be engaged. The orientation of the resilient members 12 will clearly depend upon the method of mounting the mountable bracket 1 upon the facial apparatus 6, and this will in turn influence the orientation of the camming arrangement within the bridging piece 5.

In general terms however, it is preferred for the resilient members 12 to extend upwardly from a base plate 15, in order to thereby make use of gravity in engagement between the bridging piece 5 and the mountable bracket 1.

Depending upon the nature of the facial apparatus 6 in relation to which the spectacles 2 are being utilised, the mountable bracket 1 may be fitted on an inner or outer surface thereof. For example, in the case of a breathing mask it is preferred if the mountable bracket can be fitted externally (that is, away from the patient's face) in order that the spectacles 2 can easily be engaged and disengaged without removing the mask. In other situations however, such as in the case of protective masks or goggles, it may be appropriate for the mountable bracket 1 to be fitted internally, such that the mask or goggles must be first removed before fitting or removing the spectacles therefrom.

In some instances, also depending upon the shape and configuration of the facial apparatus, it may be necessary for the length of the bridging piece 5 to he altered. For example, if a breathing mask is being utilised which has a broad section adjacent to the nose, a longer bridging piece may need to be adopted in order for the spectacles to be fitted thereabout. Also to be considered, and as would be readily apparent to a skilled optician, is the issue of vertex distance. That is, if the spectacles are going to be in place when in use, somewhat further from the eye than conventional spectacles, it may be necessary to make adjustments to the spectacle lenses in order to accommodate this. For example, an increased vertex distance results in increased magnification, so that the strength of the lenses may need to be reduced relative to the patient's normal prescription, if as a result of the configuration of the facial apparatus the spectacles will be situated further from the eye than conventional spectacles.

It has additionally been found by the present inventor that reduced base curve of lenses is often appropriate in the situation where spectacles will be located somewhat further from the eye than is conventional. The reason for this is that standard base curve, when used with increased vertex distance tends to result in distortion around the edges of the field of view. Such problems can easily be overcome by reducing the base curve and possibly also the thickness of the lens. Such adjustments however, would be readily apparent to a skilled optician.

Figures 4, 5:
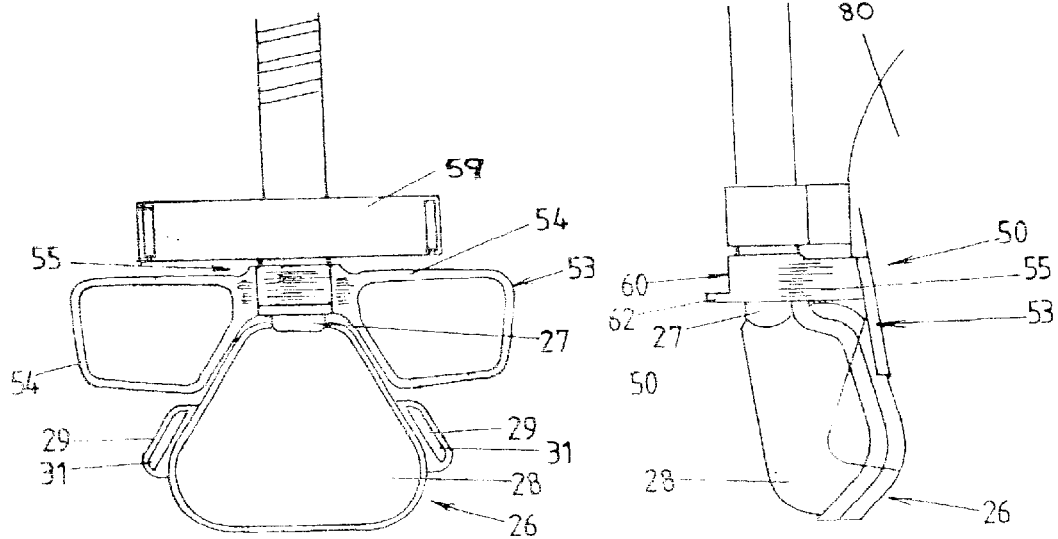
Figure 6:
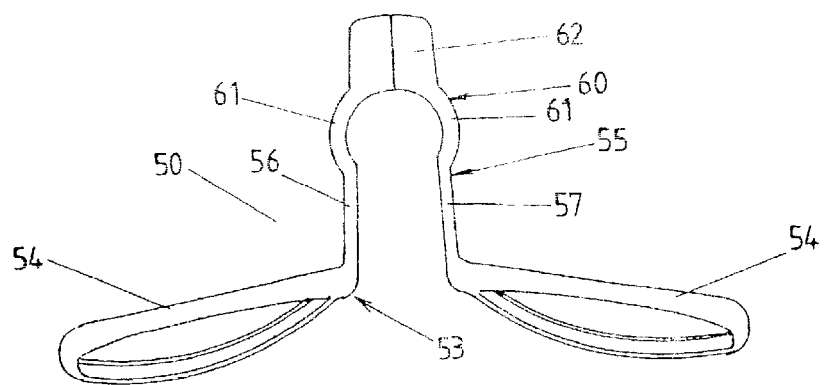
FIG. 6 is a plan view of eyewear of the type shown in FIG. 4 and 5.

Another embodiment of eyewear assembly is shown in FIGS. 4 and 5. The eyewear is shown fitted to a facial mask 26 which includes an air vent 27 and reservoir 28. Side projections 29 having slits 31 thereon are adapted to receive a mounting strap for fitting the mask to the face of the user 80 (FIG. 5). A member 59 is adapted to rest against the user's forehead when the mask is in the fitted position.

The eyewear assembly 50 is in the form of spectacles and includes a frame 53 which includes lens receiving sections 54 interconnected by a bridging piece 55. The bridging piece 55 includes a pair of arms 56 and 57 connected to respective sections 54 and a mounting bracket 60 which is an integral part of the bridging piece 55 and includes a pair of curved resilient arms 61 which are adapted to snap fit to the air vent 27. The arms 56 and 57 are connected at one end to a respective one of the lens receiving sections and are spaced apart from one another so as to define an access passage therebetween. As shown the arms extend laterally away from the user when in the fitted position. The arms 56 and 57 are integral with arms 61 of the mounting bracket 60, the access passage extending into the mounting zone of the bracket 60. The arms 56 And 57 together with arms 61 form resilient elements so that a section of the air vent 27 can pass through the access passage and snap fit into the mounting zone of the bracket 61. The assembly may be fronted as an integral unit such as a moulded member or the like. Flange 62 enables ready grip of the device for ready release of the bracket from the air vent 27. As best seen in FIG. 5 the lens receiving sections 54 of the frame are slightly inclined when in the normal in use position.

It is to be understood that the present invention has been described by way of example only, and that modifications and/or alterations which would be obvious to a person skilled in the art, based upon the disclosure herein, are also intended to be included within the scope and spirit of the present invention.

I claim:

1. Eyewear assembly for mounting eyewear to facial apparatus, the assembly including a spectacle body, mounting means for holding the spectacle body in a mounted position on the facial apparatus, the mounting means including a pair of resilient members adapted to co-operate with a mounting element to hold the spectacle body in the mounted position wherein said spectacle body includes a mounting cam thereon which defines said mounting element, said mounting means includes a mounting bracket which is securable to or integral with the facial apparatus with the resilient members being part of the mounting bracket and including a mounting section and the pair of resilient members each having a retaining element at their free end portions, the arrangement being such that the mounting cam is insertable into the region between the resilient members in a first orientation and is thereafter rotated to an in-use position whereupon the retaining elements inhibit ready removal of the mounting cam therefrom.

2. Eyewear assembly according to claim 1 wherein the mounting means includes a mounting bracket having a mounting section, said resilient members forming part of the mounting section and being adapted to snap fit onto a section of the facial apparatus which defines said mounting element.

3. Eyewear assembly according to claim 2 wherein said spectacle body includes a spectacle frame which includes two viewing sections which are interconnected by said resilient members.

4. Eyewear assembly according to claim 3 wherein said resilient members extend from respective viewing section and terminate in a region which defines a mounting zone for receiving the mounting element therein in snap fit fashion.

5. Eyewear assembly according to claim 4 further including a gripping tab in the region off said mounting zone.

6. Eyewear assembly according to claim 4 wherein the viewing sections of the spectacle body are disposed generally in a plane which, when the spectacle body is in a fitted position is inclined with respect to an upright position.

7. Eyewear assembly according to claim 3 wherein the viewing sections of the spectacle body are disposed generally in a plane which, when the spectacle body is in a fitted position is inclined with respect to an upright position.

8. Eyewear assembly according to claim 1 wherein the spectacle body includes a spectacle frame having two viewing sections and the bridge section which extends between the viewing sections.

9. Eyewear assembly according to claim 8 wherein the mounting cam is defined by the bridge section.

10. An eyewear assembly for mounting eyewear to facial apparatus, the assembly including a spectacle body and a mounting bracket for holding the spectacle body in a mounted position on the facial apparatus, the spectacle body having a bridge section which. defines a mounting cam and the mounting bracket including a mounting section which is securable to or integral with the facial apparatus and a pair of resilient members each having a retaining element at a free end portion thereof, the arrangement being such that the mounting cam is insertable into a region defined between said resilient members in a first orientation and is thereafter rotated to an in-use position whereupon the retaining elements inhibit ready removal of the mounting cam therefrom.

* * * * *